United States Patent
Lawson et al.

(10) Patent No.: US 9,867,761 B2
(45) Date of Patent: Jan. 16, 2018

(54) COLORED LAMELLAR COMPOSITIONS

(71) Applicant: L Star Softcoat, LLC, Macon, GA (US)

(72) Inventors: William R. Lawson, New Smyrna Beach, FL (US); James M. Wells, III, Macon, GA (US)

(73) Assignee: L Star Softcoat, LLC, Macon, GA (US)

( * ) Notice: Subject to any disclaimer, the term of this patent is extended or adjusted under 35 U.S.C. 154(b) by 97 days.

(21) Appl. No.: 14/699,175

(22) Filed: Apr. 29, 2015

(65) Prior Publication Data

US 2015/0313814 A1 Nov. 5, 2015

Related U.S. Application Data

(60) Provisional application No. 61/986,469, filed on Apr. 30, 2014.

(51) Int. Cl.

| | | |
|---|---|---|
| *A61K 8/02* | (2006.01) | |
| *C09B 63/00* | (2006.01) | |
| *C09C 1/40* | (2006.01) | |
| *A61K 8/25* | (2006.01) | |
| *A61K 8/46* | (2006.01) | |
| *A61K 8/49* | (2006.01) | |
| *A61K 8/26* | (2006.01) | |
| *A61K 8/58* | (2006.01) | |
| *A61K 8/81* | (2006.01) | |
| *A61Q 1/02* | (2006.01) | |
| *A61K 8/31* | (2006.01) | |
| *A61Q 1/08* | (2006.01) | |
| *A61Q 1/06* | (2006.01) | |
| *A61Q 1/10* | (2006.01) | |
| *A61Q 5/06* | (2006.01) | |
| *A61Q 9/02* | (2006.01) | |
| *A61Q 3/02* | (2006.01) | |
| *A61Q 5/02* | (2006.01) | |
| *A61Q 19/00* | (2006.01) | |
| *A61Q 1/12* | (2006.01) | |
| *B05D 3/00* | (2006.01) | |
| *A61Q 3/04* | (2006.01) | |
| *C09C 3/08* | (2006.01) | |
| *B05D 1/02* | (2006.01) | |

(52) U.S. Cl.
CPC .......... *A61K 8/0241* (2013.01); *A61K 8/0258* (2013.01); *A61K 8/25* (2013.01); *A61K 8/26* (2013.01); *A61K 8/31* (2013.01); *A61K 8/466* (2013.01); *A61K 8/494* (2013.01); *A61K 8/498* (2013.01); *A61K 8/585* (2013.01); *A61K 8/8152* (2013.01); *A61Q 1/02* (2013.01); *A61Q 1/06* (2013.01); *A61Q 1/08* (2013.01); *A61Q 1/10* (2013.01); *A61Q 1/12* (2013.01); *A61Q 3/02* (2013.01); *A61Q 3/04* (2013.01); *A61Q 5/02* (2013.01); *A61Q 5/06* (2013.01); *A61Q 5/065* (2013.01); *A61Q 9/02* (2013.01); *A61Q 19/007* (2013.01); *B05D 1/02* (2013.01); *B05D 3/007* (2013.01); *C09B 63/00* (2013.01); *C09C 1/405* (2013.01); *A61K 2800/412* (2013.01); *A61K 2800/43* (2013.01); *A61K 2800/623* (2013.01); *C01P 2004/61* (2013.01); *C09C 3/08* (2013.01)

(58) Field of Classification Search
None
See application file for complete search history.

(56) References Cited

U.S. PATENT DOCUMENTS

| | | | |
|---|---|---|---|
| 3,926,659 A | 12/1975 | Bernhard et al. | |
| 5,120,531 A * | 6/1992 | Wells | A61K 8/37 424/70.11 |
| 5,356,617 A * | 10/1994 | Schlossman | A61K 8/0204 424/401 |
| 5,931,996 A * | 8/1999 | Reisser | A61Q 1/02 106/31.65 |
| 6,406,685 B1 | 6/2002 | Philippe et al. | |
| 7,030,985 B2 | 4/2006 | Jager-Lezer et al. | |
| 7,455,847 B1 * | 11/2008 | Brown | A61K 8/06 424/400 |
| 8,349,067 B2 | 1/2013 | Hollman et al. | |
| 8,475,846 B2 | 7/2013 | Jones et al. | |
| 8,529,876 B2 | 9/2013 | Choi | |
| 8,551,188 B2 | 10/2013 | Lalleman et al. | |
| 8,647,429 B2 | 2/2014 | Melson et al. | |
| 2004/0044119 A1 * | 3/2004 | Etzrodt | B32B 27/08 524/543 |
| 2004/0156806 A1 * | 8/2004 | Patil | A61Q 1/06 424/70.12 |
| 2006/0067906 A1 * | 3/2006 | Sanders | A61K 8/37 424/70.12 |
| 2008/0202750 A1 * | 8/2008 | Rediger | C09K 8/805 166/280.2 |
| 2011/0159060 A1 | 6/2011 | Khan et al. | |
| 2013/0259914 A1 | 10/2013 | Chirayil et al. | |
| 2013/0309285 A1 | 11/2013 | Matsufuji et al. | |

* cited by examiner

Primary Examiner — Robert A. Wax
Assistant Examiner — Caralynne E Helm
(74) Attorney, Agent, or Firm — Myers Bigel, P.A.

(57) ABSTRACT

The present invention relates to a process for preparing a colored lamellar composition that may provide a wide range of colors. The process includes the steps of dispersing a colorant in a hydrocarbon, grinding the dispersed colorant to a particle size of less than about 1 micron (μm), and spraying the colorant onto a lamellar substrate to provide the colored lamellar composition while mixing and heating the lamellar composition to remove the hydrocarbon.

7 Claims, No Drawings

COLORED LAMELLAR COMPOSITIONS

CROSS-REFERENCE TO RELATED APPLICATION

This application claims priority to U.S. Provisional Application Ser. No. 61/986,469, filed Apr. 30, 2014, the disclosure of which is incorporated herein by reference in its entirety.

FIELD OF THE INVENTION

The present invention relates generally to lamellar compositions, and more particularly to a process for providing a colored lamellar composition suitable for use in the cosmetic industry.

BACKGROUND OF THE INVENTION

Compositions that can be described as "lamellar" generally have a particle morphology that is in the form of fine layers of flakes or plates. Exemplary lamellar compositions include mica, sericite, kaolin, platy alumina, glass flake, and the like.

Although such lamellar compositions are sometimes used in cosmetic or paint formulations, the ability of such lamellar compositions to provide a product with a variety of different colors is limited. As such, cosmetic formulations comprising lamellar compositions are often limited in their choice of color and shade adjustment. Thus, in order to provide a wider range or variety of colors, such as may be required in, for example, the cosmetic industry, formulations are required to use raw pigments, dyes or lakes to add color or change the color of such formulations. Thus there remains a need for a lamellar composition in a formulation wherein the end product provides a wide variety of colors that is ready to use.

Additionally, the current state of the art for organic pigments used in cosmetics is limited by current regulation defined by the Food and Drug Act. These regulations restrict how a pigment and a lake can be made and what substrates can be used. For example, the Food and Drug Act requires that a lake of an FD&C dye be made on alumina using aluminum as the laking salt. This creates a problem in formulation of a cosmetic whereby mixing pigments and extenders of different hardness, because blending then grinding creates problems with uniform grinding of color and particle size.

SUMMARY OF THE INVENTION

The present invention allows for use of these pigments and lakes with various substrates and if desirable, surface treatments. This invention uses a dye, pigment or a lake that was dispersed in a hydrocarbon and then ground to a desired particle size and then added to a substrate and then evaporating the hydrocarbon. The dispersion is made by mixing the dye, pigment or a lake then grinding on media or a sand mill, to a desired Hegman number or desired particle size. The dispersion is sprayed onto a substrate that is being mixed in a "V" cone blender with intensifier bar, or a plow blade or ribbon blender. The dispersion is added in small amounts, blended and then heated to evaporate the hydrocarbon. The process is repeated until the desired color is achieved, or the color thickness obtained. If a surface treatment of the pigment is required, the treatment can be added as the last step or it can be added as the color is added by dissolving the surface treatment into the hydrocarbon dispersion. The preferred particle morphology is lamellar, so this invention is readily suitable for mica, sericite, kaolin, platy alumina, glass flake or other lamellar particles but it is not limited to this particle morphology. This invention works equally well on spherical and acicular particles as well as pigmentary aggregates or agglomerates. Once the composite pigment is made, it easily added to formulations by blending or mixing.

The present invention and its use by cosmetic manufacturers can significantly reduce the cost of cosmetic compounding by reducing processing complexity, time and waste. The often problematic pigment grinding and pulverizing steps commonly necessary for the development of a desired cosmetic product color can be eliminated or greatly reduced by using the present invention, which, by allowing very efficient use of pre-dispersed cosmetic colorants, will simplify processing, saving money and time.

Thus, in an aspect of the present invention, provided is a process for providing a colored lamellar composition. The process includes the steps of dispersing a colorant in a hydrocarbon, grinding the dispersed colorant to a particle size of less than 1 micron ($\mu$m), and spraying the colorant onto a lamellar substrate to provide the colored lamellar composition while mixing and heating the lamellar composition to remove the hydrocarbon.

The lamellar composition provided by the process of the present invention is useful in paints, coatings, inks, and particularly cosmetic formulations. Thus, further aspects of the present invention include paints, coatings, inks and cosmetic formulations comprising colored lamellar compositions provided by the process of the invention.

In another aspect of the present invention, provided are cosmetic formulations in combination with the colored lamellar composition or compositions provided by the process of the present invention.

DETAILED DESCRIPTION OF EMBODIMENTS OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Thus, according to embodiments of the present invention are processes for providing a colored lamellar composition. In one embodiment, the process comprises the steps of dispersing a colorant in a hydrocarbon, grinding the dispersed colorant to a particle size of less than about 1 micron (μm), and spraying the colorant onto a lamellar substrate to provide the colored lamellar composition while mixing and heating the lamellar composition to remove the hydrocarbon.

The term "colorant" encompasses dyes, pigments, lakes, and mixtures thereof. Suitable colorants include any organic or inorganic pigment or colorant approved for use in cosmetics by CTFA and the FDA such as lakes, iron oxides, titanium dioxide, iron sulfides or other conventional pigments used in cosmetic formulations. Exemplary specific colorants include but are not limited to FD&C Yellow 5 lake, D&C Red 34 and D&C Red 27. The colorant should be readily dispersible in a hydrocarbon.

Exemplary dyes may be natural or synthetic. Suitable dyes for the present invention include but are not limited to: Sudan red III; lutein; quinizarin green; alizurol purple; FD&C Blue No. 11; FD&C Blue No. 12; FD&C Green No. 13; FD&C Red No. 13; FD&C Red No. 140; FD&C Yellow No. 15; FD&C Yellow No. 16; D&C Blue No. 14; D&C Blue No. 19; D&C Green No. 15; D&C Green No. 16; D&C Green No. 18; D&C Orange No. 14; D&C Orange No. 15; D&C Orange No. 110; D&C Orange No. 111; D&C Orange No. 117; FD&C Red No. 14; D&C Red No. 16; D&C Red No. 17; D&C Red No. 18; D&C Red No. 19; D&C Red No. 117; D&C Red No. 119; D&C Red No. 121; D&C Red No. 122; D&C Red No. 127; D&C Red No. 128; D&C Red No. 130; D&C Red No. 131; D&C Red No. 134; D&C Red No. 139; FD&C Red No. 140; D&C Violet No. 12; D&C Yellow No. 17; Ext. D&C Yellow No. 17; D&C Yellow No. 18; D&C Yellow No. 111; D&C Brown No. 11; Ext. D&C Violet No. 12; D&C Blue No. 16; D&C Yellow No. 110; and mixtures and blends thereof. Such dyes are well known, commercially available materials, with their chemical structure being described, e.g., in 21 C. F. R. Part 74 (as revised Apr. 1, 1988) and the CTFA Cosmetic Ingredient Handbook, (1988), published by the Cosmetics, Toiletry and Fragrances Association, Inc. Examples of vat dyes include, but are not limited to, Red No. 226, Blue No. 204 and Blue No. 201.

Pigments may be white or colored, organic or inorganic. Exemplary inorganic pigments include but are not limited to: D&C Red 7; calcium lake; D&C Red 30; talc lake; D&C Red 6; barium lake; russet iron oxide; yellow iron oxide; brown iron oxide; red iron oxide; titanium, zirconium or cerium dioxides; zinc, iron or chromium oxides; ferric blue; chromium hydrate; carbon black; polysulfides of aluminum silicates; magnesium silicate; manganese violet; manganese pyrophosphate; and metal powders (e.g., silver or aluminum powders, and mixtures and blends thereof). Exemplary organic pigments include but are not limited to Red No. 202, Red No. 204, Red No. 205, Red No. 206, Red No. 219, Red No. 228, Red No. 404, Yellow No. 205, Yellow No. 401, Orange No. 401 and Blue No. 404.

Exemplary lakes may be based on cochineal carmine, aluminum salts, barium salts, calcium salts, strontium salts, acid dyes, and mixtures and blends thereof. Exemplary lake dyes include various acid dyes, which are laked with, for example, aluminum, barium, calcium and strontium. Non-limiting examples of lakes of the present invention are Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake, Red 30 Talc Lake, and Red 30 Aluminum Lake.

Exemplary hydrocarbons may include but are not limited to about $C_5$ to about $C_{30}$, about $C_5$ to about $C_{22}$, or about $C_7$ to about $C_{16}$ linear or branched alkane, cycloalkane, an alcohol of any thereof, or blends or co-mixtures thereof. In an embodiment, the hydrocarbon is selected so that the colorant is easily dispersed therein, does not alter the properties of the colorant and may be easily removed by, for example, evaporation using heat. Additionally, the hydrocarbon is selected to avoid imparting undesirable properties to the end use product. For example, if the end use product is a cosmetic formulation, the hydrocarbon is selected to be odorless and considered safe for contact with skin. Exemplary $C_5$ to $C_{30}$ linear alkanes include but are not limited to pentane, hexane, heptanes, octane, nonane, decane, undecane, dodecane, tridencane, tetradecane, pentadecane, hexadecane, heptadecane, octadecane, nonadecane, icosane, henicosane, docosane, tricosane, tetracosane, pentacosane, hexacosane, heptacosane, octacosane, nonacosane and triacontane. Exemplary branched alkanes can include any isomer of any of these linear alkanes. In one embodiment, the branched alkane is selected from the group consisting of isododecane, isohexadecane, isoeocosane, 2,2,4-trimethylpentane 2,3-dimethylhexane, and mixtures and blends thereof. In a particular embodiment, the hydrocarbon is isododecane.

In another embodiment, cyclomethicones, dimethicones, and silicone fluids may be used as the dispersing agent.

The dispersed colorant may be then mixed well using a conventional mixer (e.g., Lady or Cowells) then ground in a media mill or sand mill to a particle size of about 1 μm or less, about 0.5 μm or less, about 0.2 μm or less, about 0.1 μm or less, less than about 0.05 μm or less, less than about 0.02 μm or less, or even about 0.01 μm or less, and sometimes between about 250 nm to about 500 nm. In a particular non-limiting embodiment, the dispersed colorant is ground to a particle size with a Hegman number of 8 or greater. The ground dispersion is sprayed onto the lamellar substrate using conventional spray techniques.

The lamellar substrate may be mica, glass flake, kaolin, sericite, platy alumina, platy iron oxides, platy silica, and pearlescent pigments. In one embodiment, suitable types of mica include muscovite, plhogopite, biotite, and synthetic mica. In another embodiment, the lamellar substrate may be polymethylmethacrylate (PMMA) microspheres.

In one embodiment, the lamellar substrate is being mixed while the dispersed colorant is sprayed. Suitable mixing vessels include a v-cone blender with intensifier bar or a plow blade or ribbon blender. Additionally the dispersed colorant may be added in small amounts, blended, and heated to evaporate the hydrocarbon. Exemplary temperatures are from about 50° C. to about 300° C., or from about 60° C. to about 260° C. The process is repeated until the preselected color and/or the desired thickness of the colorant is achieved. The range of the colorant thickness is from about 1 to about 150 nm, and in some embodiments, the colorant thickness is about 100 nm or less.

The colored lamellar composition may include a surface treatment by adding such a component as the last step or may be added to the colorant. For example, methicone may be added to make the surface of the pigment hydrophobic.

The colored lamellar composition resulting from embodiments of the present invention may be used in paints, coatings, inks, and cosmetic compositions or formulations. In one embodiment, the resulting colored lamellar composition is used in a cosmetic formulation. The form of the cosmetic formulation is not particularly limited and may be any form typically used for cosmetics such as, for example, a cream, emulsion, foam, gel, lotion, milk, mousse, ointment, paste, powder, spray, or suspension. The cosmetic composition or formulation may be any colored cosmetic used on the skin, hair, eyes, or lips, such as concealing sticks, foundation, stage make-up, mascara (cake or cream), eye shadow (liquid, pomade, powder, stick, pressed or cream), hair color, lipsticks, lip gloss, kohl pencils, eye liners, blushers, eyebrow pencils, and cream powders. Other exemplary cosmetic compositions include, but are not limited to, nail enamel, skin glosser stick, hair sprays, face powder, leg-makeup, insect repellent lotion, nail enamel remover, perfume lotion, and shampoos of all types (gel or liquid). In addition, the claimed compositions may be used in shaving cream (concentrate for aerosol, brushless, lathering), hair groom, cologne stick, cologne, cologne emollient, bubble bath, body location (moisturizing, cleansing, analgesic, astringent), after shave lotion, after bath milk and sunscreen lotion.

The present invention will be further illustrated by the following non-limiting examples.

EXAMPLES

Example 1

300 grams of FD&C Yellow 5 lake is added to 700 grams of isododecane. The pigment is then mixed well then ground in a media mill using 0.8 mm media to a hegman gage reading of 8-9. To 1 kilo of 25 μm average particle size mica, 200 grams of the FD&C Yellow 5 lake is sprayed onto the mica, then blended, and heated to remove the solvent and than pigment is dry. The process is repeated until all so the dispersion is added. The resulting pigment is bright yellow on mica which is easily dispersible in oils, silicone fluids or other suitable fluids.

Example 2

4 kilograms D&C Red 34 is added to 6 kilograms of isododecane. The pigment is then mixed well using Kady or Cowells mixer then ground in a media mill using 0.4 mm media to a hegman gage reading of >9. To 25-kilo of kaolin in ribbon blade or a plough blade mixer, 2 kilograms of D&C Red 34 dispersion is sprayed onto the kaolin, then blended, and heated to remove the solvent and the pigment is dry. To two separate 2-kg samples of the D&C Red 34 dispersion, 1 kilogram of triethoxy caprylyl silane is added and blended into the dispersion. The first 2 kilograms of D&C Red 34 dispersion is sprayed onto the kaolin, then blended, and heated to remove the solvent and the pigment is dry. The process is repeated with the second portion of the dispersion, blended, heated to 210-240° F. until the pigment is dry. The resulting red pigment is an easily dispersible hydrophobic pigment suitable for cosmetic use.

Example 3

Example 1 is repeated, however the mica is replaced by using 10 μm PMMA spheres.

Example 4

Example 2 is repeated, however the mica is replaced by using 3 μm silica spheres.

Example 5

3 kilograms of D&C Red 27 is added to 7 kilograms of isododecane. The pigment/hydrocarbon mixture is then mixed well then ground in a media mill using 0.4 mm media to a prescribed particle size finer than 1 μm. Once the dispersion has been prepared, 3 kilograms of methicone is added to the dispersion and mixed well. The dispersion-methicone mixture is added in three parts to 50 kilograms of a red iron oxide than is being mixed in a plow blade mixer. After each addition the pigment is heated to evaporate the hydrocarbon. The process is repeated until the third addition is made. Once the third addition is completed the pigment is heated to 190-195° C. for 6 hours to cure the methicone. The resulting pigment is brilliant red pigment that is extremely hydrophobic.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A process for providing a colored lamellar composition comprising the steps of:
   a) dispersing a colorant in a dispersing agent selected from the group consisting of cyclomethicones, dimethicones, and silicone fluids;
   b) grinding the dispersed colorant to a particle size of less than about 1 micron (μm); and
   c) applying the dispersed colorant onto a lamellar substrate to provide the colored lamellar composition while mixing and heating the lamellar composition to remove the dispersing agent.

2. The process of claim 1, wherein the lamellar substrate is selected from the group consisting of mica, glass flake, kaolin, sericite, platy alumina, platy iron oxides, platy silica, and pearlescent pigments.

3. The process of claim 1, wherein the colorant is selected from the group consisting of a dye, pigment, or lake.

4. The process of claim 1, wherein dispersing the colorant comprises dispersing the colorant in the dispersing agent and a hydrocarbon or an alcohol thereof.

5. The process of claim 4, wherein the hydrocarbon is a $C_5$ to $C_{30}$ linear or branched alkane, cycloalkane, or an alcohol thereof, or blends or co-mixtures thereof.

6. The process of claim 4, wherein the hydrocarbon is a $C_5$ to $C_{30}$ alkane selected from the group consisting of isododecane, isohexadecane, isoeocosane, 2,2, 4-trimethylpentane 2, 3-dimethylhexane, and blends and co-mixtures thereof.

7. The process of claim 1, wherein applying the dispersed colorant onto the lamellar substrate comprises spraying the dispersed colorant onto the lamellar substrate.

\* \* \* \* \*